United States Patent
Dastoor et al.

(10) Patent No.: US 10,978,653 B2
(45) Date of Patent: Apr. 13, 2021

(54) CHEMICAL SENSOR

(71) Applicant: Life Science Biosensor Diagnostics Pty Ltd, Sydney (AU)

(72) Inventors: Paul Dastoor, New South Wales (AU); Warwick Belcher, New South Wales (AU)

(73) Assignee: LIFE SCIENCE BIOSENSOR DIAGNOSTICS PTY LTD, Sydney (AU)

(*) Notice: Subject to any disclaimer, the term of this patent is extended or adjusted under 35 U.S.C. 154(b) by 0 days.

(21) Appl. No.: 16/313,660

(22) PCT Filed: Jun. 28, 2016

(86) PCT No.: PCT/AU2016/050555
§ 371 (c)(1),
(2) Date: Dec. 27, 2018

(87) PCT Pub. No.: WO2018/000012
PCT Pub. Date: Jan. 4, 2018

(65) Prior Publication Data
US 2019/0229284 A1    Jul. 25, 2019

(51) Int. Cl.
*H01L 51/05*        (2006.01)
*C12Q 1/00*         (2006.01)
(Continued)

(52) U.S. Cl.
CPC .......... *H01L 51/0545* (2013.01); *C12Q 1/001* (2013.01); *G01N 27/3272* (2013.01);
(Continued)

(58) Field of Classification Search
CPC ... H01L 51/0545; H01L 51/055; H01L 51/56; C12Q 1/001; G01N 27/3272; G01N 27/4145
(Continued)

(56) References Cited

U.S. PATENT DOCUMENTS 5,250,439 A * 10/1993 Musho ................ C12Q 1/002
                                                    204/403.11
9,709,560 B2 * 7/2017 Horesh ............ G01N 33/54373
(Continued)

FOREIGN PATENT DOCUMENTS

TW         201338230 A    9/2013

OTHER PUBLICATIONS

Elkington, Daniel, et al. "Organic thin-film transistor (OTFT)-based sensors." Electronics 12 (2014): 234-254.
(Continued)

*Primary Examiner* — Tu-Tu V Ho
(74) *Attorney, Agent, or Firm* — Tarolli, Sundheim, Covell & Tummino LLP

(57) ABSTRACT

A transistor device (10) is disclosed comprising a source electrode (14) a drain electrode (12) and an enzyme (31) for facilitating generation of a charge carrier from an analyte. The transistor device also comprises a polymer layer (30) for retaining the enzyme (31), the polymer layer (30) being conductive to the charge carrier. The device also comprises an ohmic conductor (32) in contact with said polymer layer (30) for applying a gate voltage to said polymer layer (30). The device also comprises an organic semiconducting layer (18) connecting the source electrode (14) to the drain electrode (12). Also disclosed is a method of making and using the device (10).

24 Claims, 13 Drawing Sheets

(51) Int. Cl.
*G01N 27/327* (2006.01)
*G01N 27/414* (2006.01)
*H01L 51/56* (2006.01)

(52) U.S. Cl.
CPC ....... *G01N 27/4145* (2013.01); *H01L 51/055* (2013.01); *H01L 51/56* (2013.01)

(58) Field of Classification Search
USPC .......................................................... 257/40
See application file for complete search history.

(56) References Cited

U.S. PATENT DOCUMENTS

| | | |
|---|---|---|
| 2015/0037827 A1 | 2/2015 | Dastoor et al. |
| 2017/0157583 A1* | 6/2017 | Kulkarni ................... B01J 2/16 |

OTHER PUBLICATIONS

Elkington, D., et al. "Printable organic thin film transistors for glucose detection incorporating inkjet-printing of the enzyme recognition element" Applied Physics Letters 106.26 (2015): 64_1.

PCT International Search Report and Written Opinion for corresponding International Application Serial No. PCT/AU2016/050555, dated Aug. 15, 2016, pp. 1-7.

Elkington, Daniel et al, "Detection of saliva-range glucose concentrations using organic thin-film transistors" Applied Physics Letters, 105, 034430, 2014 (Elkington2014).

Elkington, Daniel et al, "Review Organic Thin-Film Transistor (OTFT)-Based Sensor" Electronics 2014 3, 234-254 (Elkington2014_1).

Liao, C et al, "Organic Semiconductors in Organic Thin-Film Transistor-Based Chemical and Biological Sensors" Polymer Reviews 53:3 352-406, 2013 (Liao2013).

Darwis et al, "Novel low voltage and solution processable organic thin film transistors based on water dispersed polymer semiconductor nanoparticulates" Journal of Colloid and Interface Science, 401, 65-69, 2013 (Darwis2013).

Yan, H et al, "A high-mobility electron-transporting polymer for printed transistors" Nature 475, 5, 2009 (Yan2009).

Liu, J. et al, "Glucose sensor based on organic thin film transistor using glucose oxidase and conducting polymer" Sensors and Actuators B: Chemical 135, 195-199, 2008 (Liu2008).

Holmes, Natalie et al, "The effect of polymer molecular weight on P3HT:PCBM nanparticulate organic photovoltaic device performance" Solar Energy Materials & Solar Cells 128 369-377 2014 (Holmes2014).

* cited by examiner

CHEMICAL SENSOR

RELATED APPLICATIONS

The present application is a U.S. National Stage application under 35 USC 371 of PCT Application Serial No. PCT/AU2016/050555, filed on 28 Jun. 2016; the entirety of which is incorporated herein by reference.

FIELD OF THE INVENTION

The present invention relates to organic thin film transistors and the preparation and use thereof in sensing applications, and in particular in glucose sensing applications.

BACKGROUND OF THE INVENTION

The development of organic thin film transistors (OTFTs) has grown rapidly in recent years motivated primarily by the unique physical properties of polymer devices, including their flexibility and ability to be fabricated using low-cost, solution-based techniques. Work on developing OTFTs for new and existing applications has focussed on two main areas. First, there have been systematic improvements in the materials and fabrication processes which have led to an improvement in the conventional performance parameters of organic devices making them comparable to their inorganic counterparts. Second, improvements in film morphology of the organic semiconducting layer have been made with the goal of eliminating electron and/or hole traps and enhancing free carrier transport in the polymer semiconducting materials. Progress has also been made in developing high capacitance organic dielectric layers and large improvements in OTFT performance have been reported. The inherent compatibility of organic materials with biological molecules makes OTFTs suitable for use in biosensing applications.

The present inventors have successfully fabricated an OTFT device that is capable of analyte levels across a broad range of concentrations and which is straightforward and relatively cheap to manufacture. The device may open the way for a commercially viable glucose sensor that allows blood glucose concentration to be estimated by detecting the level of glucose in saliva as opposed to blood. Such a device may obviate the need for diabetic patients to obtain a blood sample when determining their blood glucose level. The device may also open the way for sensing of other analytes in a similar fashion.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect of the present invention there is provided a transistor device comprising:
a source electrode;
a drain electrode;
an enzyme for facilitating generation of a charge carrier from an analyte;
a polymer layer for retaining the enzyme, the polymer layer being conductive to the charge carrier;
an ohmic conductor in contact with said polymer layer for applying a gate voltage to said polymer layer; and
an organic semiconducting layer in contact with said polymer layer, the organic semiconducting layer connecting the source electrode to the drain electrode.

In at least one embodiment, a layer of the enzyme is formed on a surface of the polymer layer.

In at least one embodiment, neither said polymer layer nor said semiconducting layer include poly (4-vinylphenol) (PVP).

In a second aspect of the present invention there is provided a transistor device comprising:
a source electrode;
a drain electrode;
an enzyme for facilitating generation of a charge carrier from an analyte;
an polymer layer for retaining the enzyme, the polymer layer being conductive to the charge carrier;
an ohmic conductor in contact with said polymer layer for applying a gate voltage to said polymer; and
an organic semiconductor layer connecting the source electrode to the drain electrode;
wherein a layer of the enzyme is formed on a surface of the polymer layer.

In one embodiment, the organic semiconductor layer is in contact with said polymer layer.

In alternative embodiment, the device further comprises a dielectric layer intermediate said polymer layer and said semiconductor layer.

The dielectric layer intermediate said polymer layer and said semiconductor layer may comprise, consist of, or consist essentially of an organic dielectric material. Preferably, the organic dielectric material has a conductivity to protons that is greater than the conductivity of said semiconductor layer. Preferably the dielectric layer intermediate said polymer layer and said semiconductor layer is a homogenous layer. Preferably the organic dielectric material is a hygroscopic insulator, such as for example polyvinyl phenols. More specifically, the dielectric layer may comprise, consist of, or consist essentially of, poly(4-vinylphenol).

Alternative dielectric materials that may be used in the devices will be readily apparent to those skilled in the art. Non-limiting examples include polyimide and poly(methyl methacrylate) (PMMA). In alternative embodiments the dielectric layer may comprise a doped dielectric material, for example lithium perchlorate doped poly(4-vinylpyridine).

The dielectric layer intermediate said polymer layer and said semiconductor layer may be in contact with the organic semiconductor. Additionally or alternatively the dielectric layer may be in contact with said polymer layer.

Unless otherwise stated, the following embodiments apply to a device in accordance with any one of the above aspects of the invention.

In at least one embodiment, the organic semiconducting layer consists of one organic semiconductor.

In at least one embodiment, the organic semiconductor layer has a thickness of less than about 390 nm.

In at least one embodiment, the organic semiconductor layer has a thickness of between about 36 nm and about 9 nm. In at least one embodiment, the organic semiconductor layer has a thickness of between about 22 nm and about 9 nm.

In at least one embodiment, the organic semiconductor layer has a thickness between about 22 nm and about 390 nm. In at least one embodiment, the organic semiconductor layer has a thickness between about 74 nm and about 108 nm (such as between 75 nm and 100 nm).

Preferably said thickness spans at least between the polymer layer and inner ends of the respective source and drain electrodes, the inner ends being at opposite ends of a channel between the source and drain electrodes. However, preferably said thickness is a minimum thickness between the polymer layer and all of the source electrode and drain electrode.

The charge carrier may be any one or more of the following charge carrier types: anions, cations or electrons. However, in at least one embodiment the charge carriers are cations, and more preferably hydrogen ions (eg protons).

Preferably said polymer layer forms a proton-conductive membrane. Preferably the polymer layer has a conductivity to protons that is greater than a conductivity to protons that is possessed by said organic semiconductor layer.

In at least one embodiment, at least part of the polymer layer is disposed above the semiconductor layer. Optionally, at least part of the ohmic conductor may be beneath another part of the polymer layer.

In some embodiments, said conductivity (whether it be in respect of the polymer layer or in respect of said organic dielectric layer, if such a dielectric layer exists) is due to a permeability to said charge carriers, whereby conduction is by migration of said charge carriers. In other embodiment, said conduction may by another mechanism, such as the Grotthuss mechanism.

Preferably, the organic semiconductor is doped by interaction with said charge carriers, preferably protons, to increase an electrical conductivity between the drain electrode and the source electrode.

Preferably the polymer layer is not covered by the organic semiconductor. In at least one embodiment this is achieved by having the polymer layer as a top-most layer of the device, ie furthest from the substrate. In another embodiment this is achieved by having the polymer layer beneath the organic semiconductor, but extending laterally beyond the organic semiconductor so that a portion of the polymer layer is not covered by the semiconductor.

In at least one embodiment, an organic semiconductor in the organic semiconductor layer is in contact with the source electrode and the drain electrode. The organic semiconductor layer preferably includes is a substantially flat and planar region, but in some embodiments may include different regions having different thicknesses.

As described herein, the enzyme for use in the device according to the invention is one which facilitates the generation of a charge carrier from an analyte, the charge carriers typically being an electron, anion or cation (eg proton). The generation of the charge carriers may be further facilitated by the presence of an electric field. As will be described, these generated charge carriers can then contribute to electric current through the device. It will be recognised that a range of enzymes could be used for any one particular analyte. Further given the diversity of enzymes available, the device, by following the disclosure herein can be adapted or developed for detection of a range of analytes.

A particularly preferred class of enzyme is an oxidoreductase. An oxidoreductase for use in the device may act on any one of the following donor groups:

the CH—OH group of donors (alcohol oxidoreductases),
the aldehyde or oxo group of donors,
the CH—CH group of donors (CH—CH oxidoreductases),
the CH—NH$_2$ group of donors (Amino acid oxidoreductases, Monoamine oxidase),
CH—NH group of donors,
NADH or NADPH,
other nitrogenous compounds as donors,
a sulfur group of donors,
a heme group of donors,
diphenols and related substances as donors,
peroxide as an acceptor (peroxidases),
hydrogen as donors,
single donors with incorporation of molecular oxygen (oxygenases),
paired donors with incorporation of molecular oxygen,
superoxide radicals as acceptors,
CH or CH$_2$ groups,
iron-sulfur proteins as donors,
reduced flavodoxin as a donor,
phosphorus or arsenic in donors, or
X—H and Y—H to form an X—Y bond, or
may be oxidoreductases that oxidize metal ions.

In one embodiment, an enzyme as described herein is one enabling detection of glucose.

In another embodiment the enzyme is an alcohol oxidoreductase enabling detection of glucose. Preferably the alcohol oxidoreductase is glucose oxidase.

In at least one embodiment, the enzyme is glucose oxidase for detecting glucose.

The device may be a device for sensing an analyte in a sample. In an embodiment the analyte is glucose. The sample may be any aqueous solution but is preferably a biological fluid, more preferably a bodily fluid, and still more preferably, saliva.

Preferably at least part of the enzyme is contained within at least part of the polymer layer. In at least one embodiment, the polymer layer includes pores (or vacancies or structures) containing said at least part of the enzyme.

In some embodiments, the enzyme may be pre-mixed with and deposited together with the polymer layer. Alternatively, the enzyme is formed by depositing it on said polymer layer after depositing said polymer layer. In a further embodiment, the enzyme is pre-mixed with the polymer layer and deposited on the mixture after depositing the mixture.

Preferably, the enzyme is printed, eg ink-jet printed, on said polymer layer. Printing methods used in other embodiments include gravure, flexographic and doctor blade. However, in still other embodiments, non-printing methods known to those skilled in the art may used, such as drop casting, vapour deposition and sputtering. In at least one embodiment, a mixture of the porous matrix and the enzyme is drop cast over the organic semiconducting layer.

Preferably, the transistor also comprises a substrate. Preferably, at least the source electrode and drain electrode are disposed on the substrate. In at least one embodiment, the source electrode, drain electrode and organic semiconductor are each in contact with the substrate. The substrate may be glass, or any other suitable substrate known to those skilled in the art, for example paper or low-cost plastics, such as polyethylene terephthalate (PET).

The source electrode and the drain electrode may be disposed above the substrate. The source electrode and the drain electrode may be in contact with the semiconductor layer.

The organic semiconducting layer is preferably in contact with, the source electrode and the drain electrode. At least part of the organic semiconducting layer is disposed above the source electrode and the drain electrode. Preferably a majority of the organic semiconducting layer is disposed above the source electrode and the drain electrode.

The organic semiconductor comprises, consists, or consists essentially of at least one organic compound that has semiconducting properties. Examples of suitable organic compounds include, but are not limited to: polyacetylenes, porphyrins, phthalocyanins, fullerenes, polyparaphenylenes, polyphenylenevinylenes, polyfluorenes, polythiophenes, polypyrroles, polypyridines, polycarbazoles, polypyridinevinylenes, polyarylvinylenes, poly (p-phenylmethylvinylenes), including derivatives and co-polymers thereof, and further including mixtures thereof.

In at least one embodiment of the invention the at least one organic compound is selected from the group consisting of: poly(9,9-dioctylfluorene-2,7-diyl-co-bis-N,N-(4-butylphenyl)-bis-N,N-phenyl-1,4-phenylenediamine), poly (9,9-dioctylfluorene-2,7-diyl-co-benzothiadiazole), poly(3-hexylthiophene), (6,6)-phenyl-$C_{61}$-butyric acid methyl ester and poly(2-methoxy-5-(2'-ethyl-hexyloxy)-1,4-phenylene vinylene). Also contemplated are mixtures of one or more of the above noted organic compounds.

In at least one embodiment, the at least one organic compound is poly(3-hexyl-thiophene), ie P3HT.

The polymer layer retaining the enzyme may be porous. In the embodiment in which the enzyme is at least partly embedded within the polymer layer, it is preferable that the polymer layer is porous so that a sample (eg saliva) can permeate through the pores to contact the enzyme embedded in the polymer layer. Additionally the presence of pores may assist in anchoring the enzyme to the polymer to ameliorate removal (eg washing off) of the enzyme when contacted with a sample.

The polymer layer may comprise, consist, or consist essentially of a sulfonated tetrafluoroethylene-based fluoropolymer-copolymer, for example a copolymer comprising a tetrafluoroethylene backbone and perfluoroalkyl ether groups terminated with sulfonate groups.

The sulfonated tetrafluoroethylene-based fluoropolymer-copolymer may be a copolymer of tetrafluoroethylene and perfluoro-3,6-dioxa-4-methyl-7-octene-sulfonic acid. It is preferred that the sulfonated tetrafluoroethylene-based fluoropolymer-copolymer is a tetrafluoroethylene-perfluoro-3,6-dioxa-4-methyl-7-octenesulfonic acid copolymer which is commonly referred to as Nafion.

In an embodiment, the tetrafluoroethylene-based fluoropolymer-copolymer has the following structure:

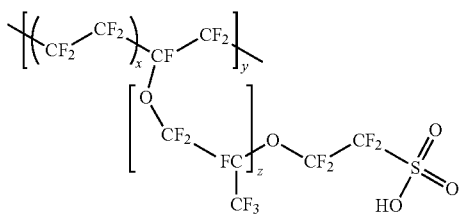

In an embodiment, the tetrafluoroethylene-based fluoropolymer-copolymer has the following structure:

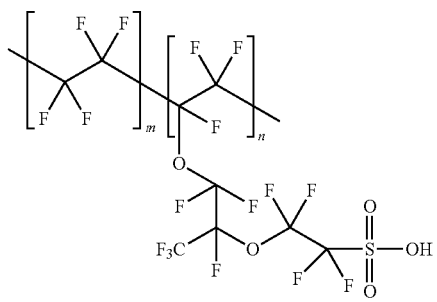

Preferably said ohmic conductor comprise, consist, or consist essentially of ITO, for example pre-patterned ITO.

Preferably each of said source and drain electrodes consist of an ohmic material. In at least one embodiment, source electrode and drain electrode each comprise, consist, or consist essentially of ITO, for example pre-patterned ITO.

As an alternative to ITO, in other embodiments the ohmic conductor, source electrode and/or drain electrode may comprise, consist, or consist essentially of a different ohmic material, such as other metals (eg gold or silver) or metal oxides, or graphene. The device may have a channel length, between the source and drain of electrodes, of between about 5 μm and about 50 μm, or between about 10 μm and about 30 μm, or about 20 μm, and a channel width of between about 1 mm and about 20 mm, or between about 1 mm and about 10 mm, or about 3 mm.

The organic semiconducting layer may have a thickness between about 5 nm and about 500 nm, or between about 75 nm and about 125 nm, or about 100 nm.

In a third aspect, the present invention provides a method for preparing a transistor device as defined in the first or second aspect of the invention, the method comprising:
 a) providing a substrate for depositing thereon components of the device;
 b) depositing the source electrode and the drain electrode;
 c) depositing the organic semiconductor;
 d) depositing the polymer; and
 e) depositing the enzyme on said polymer.

Preferably, the source electrode and the drain electrode are deposited on the substrate.

In at least one embodiment step b) precedes step c), step c) precedes step d), and step d) precedes step e).

Preferably the method also includes depositing the ohmic conductor, whereby the ohmic conductor is in contact with said polymer layer to control an electric potential of said polymer layer. Preferably, in this case, the ohmic conductor is deposited before the polymer layer for retaining the enzyme is deposited.

In other embodiments, the ohmic conductor may be connected to said polymer layer in use, to control an electric potential of said polymer layer, whereby the ohmic conductor is not integrated into device during manufacture of the device.

In at least one embodiment, the source electrode and the drain electrode are deposited over the substrate. In at least one embodiment, the organic semiconductor layer is deposited over source electrode and the drain electrode.

In at least one embodiment, the polymer is deposited over the organic semiconductor. In some embodiments, no dielectric layer is deposited. However, in the case of the method being applied to prepare a device according to the second aspect of the invention, and said device is to include said dielectric layer, said dielectric layer may be deposited over the organic semiconductor, with said polymer of the polymer layer then being deposited over the organic dielectric layer. In this case, the dielectric layer may be deposited by spin coating.

In at least one embodiment, the enzyme is introduced as part of and/or after d). In at least one embodiment, the enzyme is introduced after step d). Preferably the enzyme is introduced by ink-jet printing.

Step b) may comprise depositing the source electrode and the drain electrode over the substrate such that the source electrode and the drain electrode are disposed above, and in contact with, the substrate.

Step c) may comprise depositing the organic semiconductor over the source electrode and the drain electrode such that at least part, but preferably a majority, of the semiconductor is disposed above and in between the source electrode and the drain electrode.

Preferably, in step c), the semiconductor is deposited such that it is in contact with the source electrode and the drain electrode.

In at least one embodiment, the semiconductor layer is deposited by spin coating.

In at least one embodiment the polymer layer is deposited by spin coating.

Devices in accordance with the present invention may be fabricated by low-cost spin-coating and printing techniques, thereby offering the potential for affordable and disposable non-reversible devices for sensing glucose. All of the components of the device are capable of being printed.

The organic semiconducting layer and/or the dielectric layer (for embodiments in which such a dielectric layer is included) may be deposited in accordance with methods well known to those skilled in the art, including, but not limited to: electroplating, vapour phase deposition, spin coating, screen printing, ink-jet printing, slot-dye printing, spray coating, draw bar coating or derived coating/printing techniques thereof, painting, gravure, roller and embossing.

The organic semiconducting layer may be deposited so as to achieve a thickness between about 5 nm and about 500 nm, or between about 75 nm and about 125 nm, or about 100 nm.

In a fourth aspect, the present invention provides use of the device of the first or second aspect for sensing an analyte in a sample.

The analyte may be glucose.

The sample may be a bodily fluid, for example saliva.

In a fifth aspect, the present invention provides a method for detecting and/or determining a concentration or an amount of an analyte in a sample, the method comprising the following steps:
 a) providing a device of the first or second aspect;
 b) contacting the sample with the device; and
 c) detecting and/or determining the concentration or the amount of the analyte based on an electrical parameter of the device.

The method may comprise applying a voltage to the drain electrode with respect to the source electrode. Preferably the method also comprises applying a voltage to the ohmic conductor with respect to the source electrode. Preferably the voltage applied to the ohmic conductor (ie the "gate voltage") and the voltage to the drain electrode have the same polarity with respect to the source electrode.

The method may include detecting drain current through the device, wherein the concentration or amount of the compound is determined based on a magnitude of the drain current.

The determination of the concentration or amount may be performed by reference to an appropriate calibration curve.

The compound may be glucose.

Step b) may comprise contacting the sample with said polymer layer.

The gate voltage and drain voltage applied may be voltages greater than that required to liberate $H^+$ from $H_2O_2$, and lower than that required to cause electrolysis of water.

The gate voltage and drain voltage applied may be between about 0 V and −2 V, or about −1 V.

The sample may be a bodily fluid, for example saliva.

In a sixth aspect the present invention provides a device whenever prepared by the method of the third aspect.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

A preferred embodiment of the present invention will now be described, by way of example only, with reference to the accompanying drawings wherein.

DEFINITIONS

Figure 1:
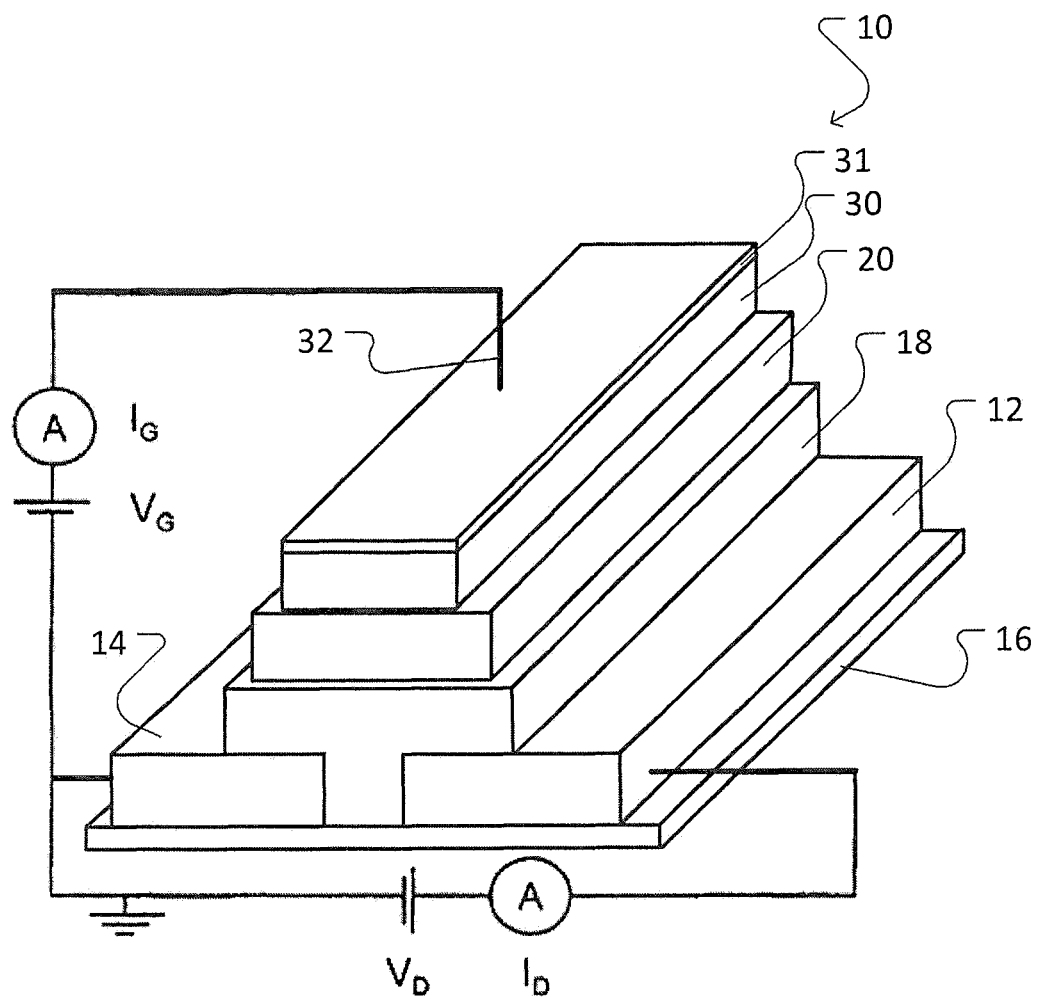
FIG. 1 shows the structure of a device in accordance with one embodiment of the invention.

The following are some definitions that may be helpful in understanding the description of the present invention. These are intended as general definitions only and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the term "about" is understood to refer to a range of numbers that a person of skill in the art would consider equivalent to the recited value in the context of achieving the same function or result.

In the context of this specification, the terms "a" and "an" refer to one or to more than one (i.e. to at least one) of the grammatical object of the article. By way of example, "an element" means one element or more than one element.

In the context of this specification, the term "bodily fluid" is understood to include any liquid which originates within a human or animal body, including fluids that are secreted or excreted. Non-limiting examples of bodily fluids include: blood, saliva, sweat, urine, breast milk, bile and peritoneal fluid.

In the context of this specification, the term "top" means farthest away from the substrate, and the term "bottom" means closest to the substrate. Where a first layer is described as "disposed above" a second layer, the first layer is disposed farther away from the substrate. Furthermore, where a first layer is described as being "disposed above" a second layer, additional intermediate layers may be present in between the first and second layers, unless it is specified that the first layer is contact with (ie physically contacting) the second layer.

As used herein, like reference numerals in different figures are intended to refer to the same features.

The invention will now be described in more detail, by way of illustration only, with respect to the following examples. The examples are intended to serve to illustrate this invention and should in no way be construed as limiting the generality of the disclosure of the description throughout this specification.

DETAILED DESCRIPTION OF THE EMBODIMENTS

An exemplary transistor device 10 in accordance with one embodiment of the invention is illustrated in FIG. 1, which includes a conceptual representation of the device's structure. The device 10 includes a drain electrode 12 and source electrode 14 on a substrate 16. A two-layered film comprised of an organic semiconducting layer 18 and a hygroscopic dielectric layer 20 covers a portion of the drain and source electrodes, with the organic semiconducting layer 18 extending between the source and drain electrodes. A polymer layer 30 is, located at the top of the device 10. An ohmic conductor 32 is in contact with the polymer layer 30 to enable a gate voltage to be applied to the polymer layer, The polymer layer 30 is disposed above and is in contact with the dielectric layer 20. The dielectric layer 20 is disposed above and is in contact with the organic semiconducting layer 18. The organic semiconducting layer 18 is disposed above and in between the source electrode 14 and the drain electrode 12. The organic semiconducting layer 18 is also in contact with the source electrode 14 and the drain electrode 12. The source electrode 14 and the drain electrode 12 are disposed above, and are in contact with, the substrate 16. The substrate 16 is located at the bottom of the device 10.

The polymer layer 30 retains an enzyme 31 such that the enzyme is embedded within and/or retained on a surface of the polymer layer. In the embodiment described herein, the polymer layer 30 is a porous layer of a sulfonated tetrafluoroethylene-based fluoropolymer-copolymer (eg Nafion). The enzyme, which may be glucose oxidase (GOX) for example, is distributed throughout the layer or is at least partially contained within the layer.

The enzyme is selected to facilitate generation of charge carriers when an analyte contacts the device and a minimum electric potential (ie gate voltage or potential) is applied to the ohmic conductor 32, the voltage being selected relative to at least one of the drain and source electrodes. The charge carriers comprise hydrogen ions and electrons. The ohmic conductor 32 applies the gate voltage to the polymer layer 30, resulting in a substantial electric field component in a vertical plane (ie in a plane perpendicular to the top surface of the semiconductor layer). The organic semiconductor is configured to enable flow of electrical current between the source electrode and the drain electrode as a result of the generation of said charge carriers.

In the devices of the present invention, it is believed that the gate potential controls the doping and de-doping of the semiconducting compound(s) via ion migration from the site of ion generation to the active channel in the organic semiconductor. In use, a gate voltage $V_G$ and a drain voltage $V_D$ are applied to the device 10 (the voltages being with respect to the source 14, as shown in FIG. 1), and a sample comprising glucose, for example a bodily fluid such as saliva, is contacted with the polymer layer 30. Glucose in the sample is degraded via an enzymatic reaction with GOX thereby producing $H_2O_2$. The gate voltage and drain voltage applied cause electrolysis of $H_2O_2$ thereby liberating $H^+$ ions. The $H^+$ ions are conducted though the polymer layer (eg Nafion) and, if present, the dielectric (eg PVP), to the organic semiconducting layer. This results in doping of the semiconductor, and consequentially, current between the drain and the source electrodes. Thus, the increase in $H^+$ ions results in an increase in drain current, such that a relationship is established between the amount of glucose present in the sample and the magnitude of the drain current.

The gate voltage $V_G$ and drain voltage $V_D$ provide a sufficiently strong electric field to liberate $H^+$ from $H_2O_2$, but not enough to cause electrolysis of water, as electrolysis of water may lead to a decrease in the signal-to-noise ratio of the sensor. In at least one embodiment, the gate voltage and drain voltage applied are between about 0 V and −2 V, eg about −1 V.

An exemplary device of the prior art is disclosed in International patent application PCT/AU2013/000207, filed 5 Mar. 2013. That patent application provides an example of organic transistor with a Nafion polymer layer and a hygroscopic dielectric layer.

However, the present inventors have identified that the device can operate effectively without a hygroscopic dielectric layer between the polymer layer and the organic semiconductor layer.

Further the inventors of the present patent application have identified advantageous device behaviour by incorporating the enzyme into the device after depositing the polymer layer. Advantageously, the enzyme may be deposited by ink-jet printing, potentially improving manufacturing costs, at least for manufacturing setup.

Further the inventors of the present invention have identified that the device operates at least for an organic semiconductor layer thickness of less than about 390 nm. Further, there is advantageous device behaviour when the organic semiconducting layer has a thickness in the range of about 75 nm and about 100 nm, between the polymer layer 30 and the source and drain electrodes. The advantage is that in this range the inventors have identified that the device has a calibration curve that has a one-to-one correspondence between a calibration parameter and glucose concentration for concentrations between 0.1 mM and 100 mM. Further their results have shown the calibration curve as being is essentially linear over that range.

Further, there is also advantageous device behaviour when the organic semiconducting layer instead has a thickness in the range of about 36 nm or less, between the polymer layer 30 and the source and drain electrodes. The advantage in this case is a faster response time for the device.

Figure 2:
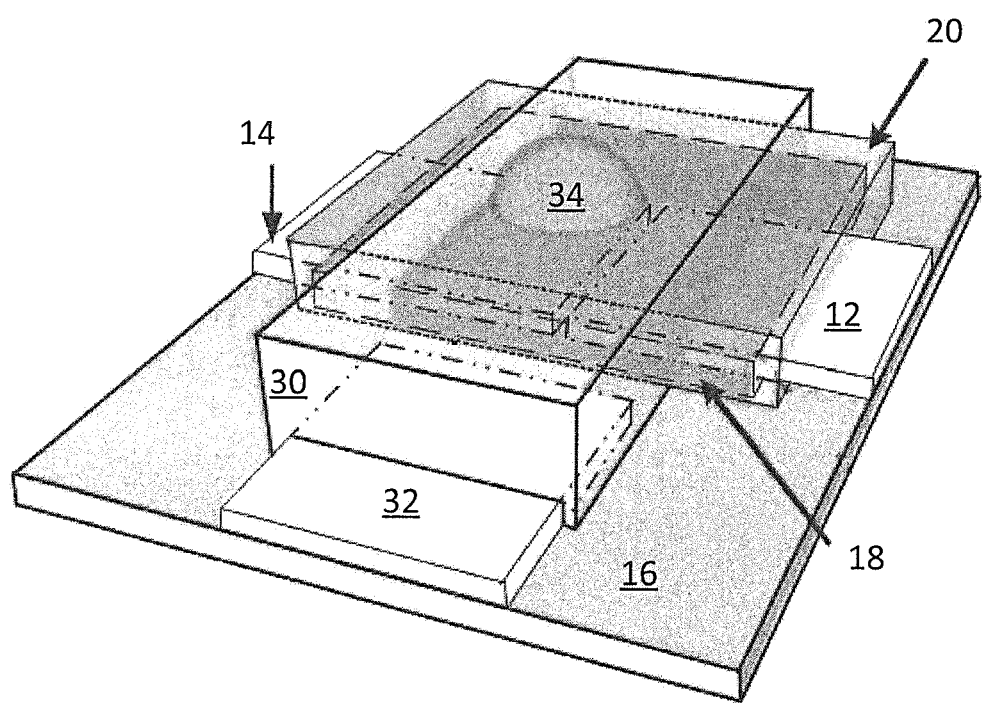
FIG. 2 shows the a perspective view (not to scale) modelling a fabrication of the device of FIG. 1.

A perspective view (not to scale) of a device 10 fabricated in accordance with the present invention is illustrated in FIG. 2. In this Figure, the source electrode 14, drain electrode 12 and ohmic conductor 32 are provided as pre-patterned ITO on the substrate 16, which is a glass slide (Kintec). A channel length of 20 μm and a width of 3 mm is provided between and covering part of the source electrode 14 and the drain electrode 12. A layer of poly (3-hexylthiophene) (P3HT) (Lumtec) with 100 nm thickness is spin-coated on top of the ITO as the organic semiconducting layer 18. Poly (4-vinylphenol) (Aldrich) is spin-coated on top of the P3HT layer with a thickness of approximately 36 nm to form the dielectric layer 20. However, in other embodiments, the Poly (4-vinylphenol) layer is thinner, and in at least one embodiment, there is no Poly (4-vinylphenol) layer. A Nafion solution (Product Number 274704—Sigma-Aldrich Pty. Ltd., Castle Hill NSW, Australia) is spin coated onto the film that the includes the semiconductor (and dielectric, in embodiments in which a dielectric is present) to form the polymer layer. The enzyme, which in this embodiment is glucose oxidise, is ink-jet printed onto the polymer layer. In some embodiments a layer of the enzyme 31 may be formed on the surface of the polymer layer 30 (as depicted in FIG. 1). However, in other embodiments, the enzyme may be additionally or alternatively absorbed at least partly into the polymer layer—hence for simplicity in FIG. 2 the polymer layer and enzyme are illustrated as a single component 30. It will therefore be appreciated, however, that the fabricated device as shown in FIG. 2 may, in some embodiments, include a layer of the enzyme 31 formed on the surface of the polymer layer 30.

The ohmic conductor 32 is laterally offset from the source and drain electrodes, as is part of the polymer layer. In use, a sample 34 (eg a person's bodily fluid) is deposited onto polymer layer 30. GOX breaks down glucose into $H_2O_2$, amongst other by-products, and the electrolysis of $H_2O_2$ occurs at a voltage magnitude of 0.7 V, which liberates $H^+$ ions. Accordingly, in order to bias the device appropriately, the voltage sufficient to liberate ions from the $H_2O_2$ should be available, but the voltage should preferably not exceed the potential difference required to cause electrolysis of water (1.23 V) which would decrease the signal-to-noise ratio of the sensor.

For glucose sensing measurements, the device was biased at $V_D = V_G = -1$ V and 10 μL of sample of the analyte in solution (various glucose concentrations in water) was dropped on top of the device (i.e. onto the polymer layer 30 which comprises the GOX) whilst $I_D$ was measured as a function of time. The $H_2O_2$ liberated by the enzymatic reaction on glucose and its subsequent electrolysis leads to additional ions in the system which has a similar effect to increasing the level of $V_G$ to achieve a higher $I_D$.

The characteristic response of a device having a prior sensor architecture—comprising ITO source drain electrodes, a P3HT organic semiconducting layer, a poly (4-vinylphenol) (PVP) dielectric layer, and a layer comprising the Nafion membrane pre-mixed with GOX—to glucose analyte solutions was disclosed in PCT/AU2013/000207. Subsequent investigations by the present inventors have shown that removing or reducing the thickness the dielectric layer can improve the response time of the sensor.

EXAMPLES

Examples illustrating various features of the present invention will now be described for a device manufactured in accordance with FIG. 2, in which the no dielectric layer is present between the polymer layer (in this case Nafion) and the organic semiconductor layer (in this case P3HT).

Figure 3A:
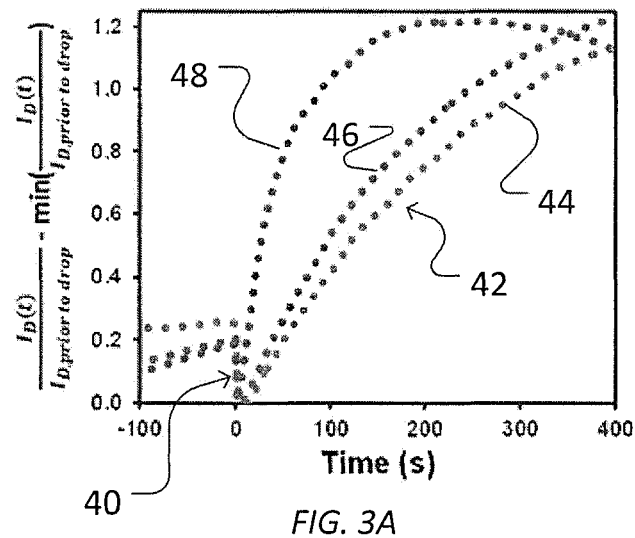
FIG. 3A shows a measure of drain current ($I_D$) vs time for the device according to FIGS. 1 and 2, with various thicknesses between the polymer layer and the drain and source, showing a fast decay followed by a slow rise in the measure of drain current.
Figure 3B:
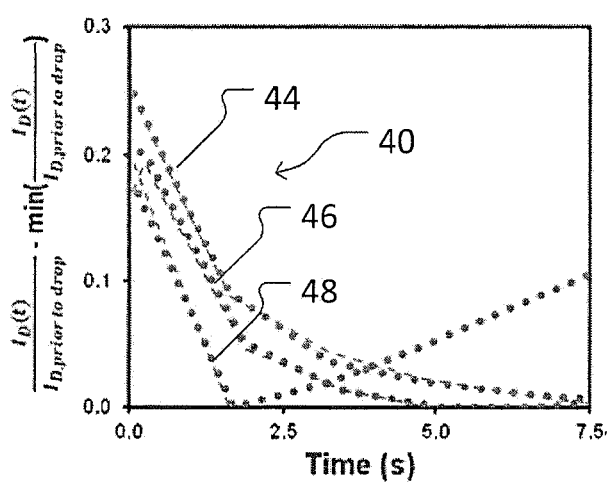
FIG. 3B is an expanded view of the fast decay shown in FIG. 3A.
Figure 3C:
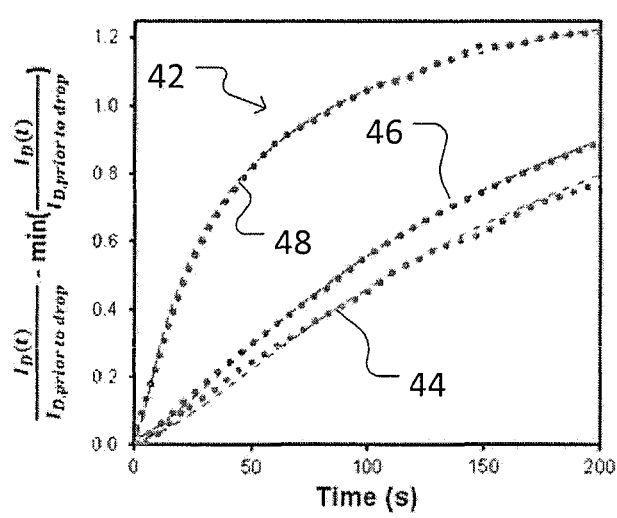
FIG. 3C is an expanded view of the slow rise shown in FIG. 3A.

FIGS. 3A-3B shows the effect of varying the thickness of the organic semiconducting layer from 108 nm to 22 nm upon the rate of sensor response, represented by drain current ($I_D$) as a function of time. FIG. 3A shows variation of $I_D$ with time for the P3HT/Nafion:GOX OTFT architecture with a P3HT layer having a thickness of 108 nm (indicated by 44), 36 nm (indicated by 46), and 22 nm (indicated by 48). The glucose solution is added at t=0 and a fast decay and a slower rise in $I_D$ is observed for all P3HT layer thicknesses. FIG. 3B shows an expanded view of the fast decay process for the P3HT/Nafion:GOX OTFT architecture for the three different thicknesses for the semiconductor layer. FIG. 3C shows an expanded view of the slow rise process for the P3HT/Nafion:GOX OTFT architecture for the three different thicknesses for the semiconductor layer.

For the sake of data clarity, $I_D$ is presented as a ratio of its stabilized level prior to addition of sample (glucose-containing saliva) minus the minimum value of this ratio (which occurs soon after sample addition)—a quantity referred to hereafter as "adjusted $I_D$."

As the thickness of the P3HT channel is reduced, it appears that the response time of a fast de-doping process 40 and a slow doping process 42 both reduce, consistent with diffusion processes that traverse a reduced layer thickness. Both processes can be modelled by one dimensional solutions to Fick's second law of diffusion, $n(x,t) = n_0 \, \text{erfc}\{x/[2/(D_{\text{eff}} t)^{0.5}]\} = n_0 \, \text{erfc}(A/t)$, where A (comprising x (diffusion distance) and $D_{\text{eff}}$ (effective diffusion constant)) and $n_0$ (initial concentration) are treated as fitting constants with the fit solution shown as dashed lines in FIGS. 3A and 3B.

Fitting the fast ($A_{fast}$) and slow ($A_{slow}$) responses to Ficks law provides an estimate for the value of A for each process where $A=x/[2(D_{eff}t)^{0.5}]$.

The fitted values of A are 0.62 (for 108 nm P3HT), 0.48 (for 36 nm P3HT), and 0.44 (for 22 nm P3HT) for the fast decay process. The fitted values of A are 10.3 (for 108 nm P3HT), 9.4 (for 36 nm P3HT), and 3.6 (for 22 nm P3HT) for the slow decay process.

It is the understanding of the present inventors that the fast dedoping and slow doping processes have to diffuse across the same layer thickness for a given OTFT architecture. As such, $A_{fast}/A_{slow}=[D_{slow}/D_{fast}]^{0.5}$, where $A_{slow}$ and $A_{fast}$ are the fitting parameters, and $D_{slow}$ and $D_{fast}$ are the effective diffusion constants, for the slow and fast processes, respectively. Thus, the ratio $A_{fast}/A_{slow}$ as a function of changing layer thickness should only depend upon the ratio of the diffusion constants of the two processes.

Figure 4A:
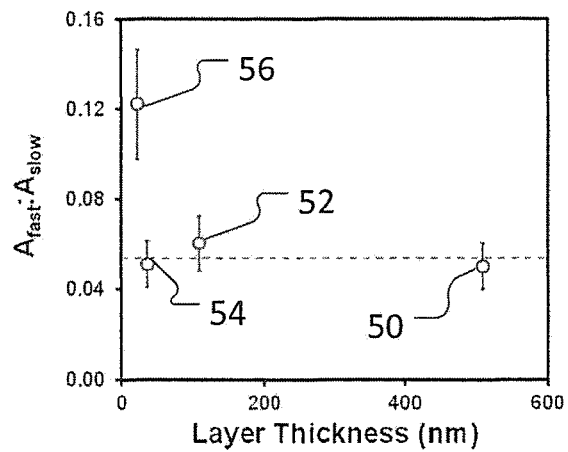
FIG. 4A shows a ratio $A_{fast}/A_{slow}$, A being a constant that is related to diffusion distance and an effective diffusion constant, for the device according to FIGS. 1 and 2, with various thicknesses between the polymer layer and the drain and source.

FIG. 4A shows the variation of $A_{fast}/A_{slow}$ as a function of the different device layer thicknesses and includes the data for both the devices with PVP (layer thickness 400 nm), as data point 50, and the devices of varying P3HT thickness without a PVP layer, as data points 52, 54, and 56. The $A_{fast}/A_{slow}$ ratio is relatively invariant across both the OTFT device with a PVP layer and the devices without a PVP layer but with P3HT layers that are at least 36 nm thick.

This observation supports the assertion that, for each OTFT architecture, the fast dedoping and slow doping process diffuse across the same effective distance and indicates that the ratio of the corresponding diffusion constants is invariant.

However, when the P3HT thickness drops below 36 nm, there is an abrupt increase in the $A_{fast}/A_{slow}$ ratio. The fitted values for A (for both the slow and fast processes) decrease with decreasing P3HT layer thickness, consistent with more rapid diffusive transport. Moreover, the decrease in $A_{slow}$ for the very thinnest P3HT layer is more dramatic than the corresponding decrease in $A_{fast}$, indicating that there is a difference in the two processes for P3HT thicknesses below about 36 nm.

Figure 4B:
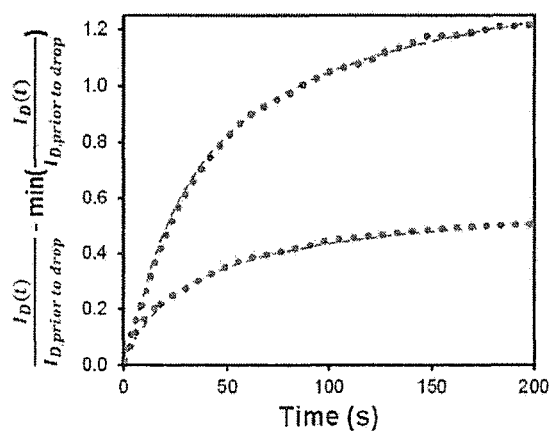
FIG. 4B illustrates a variation in the measure of drain current as a function of time for two OTFT devices, both without a PVP dielectric, and having a P3HT organic semiconducting layer having a thickness of about 22 nm and about 9 nm, respectively.

FIG. 4B illustrates the variation of $I_D$ as a function of time for non-PVP OTFT devices with a P3HT layer having a thickness of 22 nm (the upper dotted line in the figure) and about 9 nm (the lower dotted line in the figure). An examination of FIG. 4B reveals that this abrupt increase is dominated by a critical change in the effective diffusion constant for the slow doping process for P3HT thicknesses below 36 nm.

The data in FIG. 4A are consistent with the presence of some thickness of P3HT which only serves to slow the diffusion rate of protons to the active (doping) region of the channel. As such, when the P3HT thickness drops below a critical value (about 36 nm) then there is no diffusive barrier to protons accessing the doping region of the device. Indeed, this suggests that any further reduction of the P3HT layer thickness should not affect the diffusion rate of either the fast or slow process (since there is no diffusive barrier) and reducing the P3HT thickness now merely alters the absolute number of doping sites and therefore the current in the channel.

To confirm this, the P3HT layer thickness was further reduced from 22 nm by decreasing the concentration of the P3HT solution (from 5 mg mL$^{-1}$ to 2 mg mL$^{-1}$). The resulting P3HT layers exhibited regions of incomplete coverage and hence the layer thickness (about 9 nm) could only be estimated from the P3HT loading. Despite this, functional devices could be prepared. FIG. 4B compares $I_D$ as a function of time for two devices. respectively with a 22 nm and a 9 nm thick P3HT layer. FIG. 4B shows that the device response is lower for the thinner P3HT layer and that $I_D$ at saturation has reduced from a value of about 1.2 to a value of about 0.5 on this scale, corresponding to a 42% reduction in current that is quantitatively consistent with the reduced P3HT thickness. Fitting the current to the Fick's law reveals that the only fitted parameter that has to be changed is that of $n_0$ (which governs the absolute magnitude of the response), whereas the fitted value of A is constant for both fast and slow processes for both of these P3HT thicknesses. Consequently, the data are consistent with a doping region which, for thicker P3HT layers, does not lie at the interface between the P3HT and the Nafion layer but instead lies at some small distance from the source and drain electrodes and is overlayed by undoped P3HT through which protons must diffuse (or conducted in some other way).

Figure 4C:
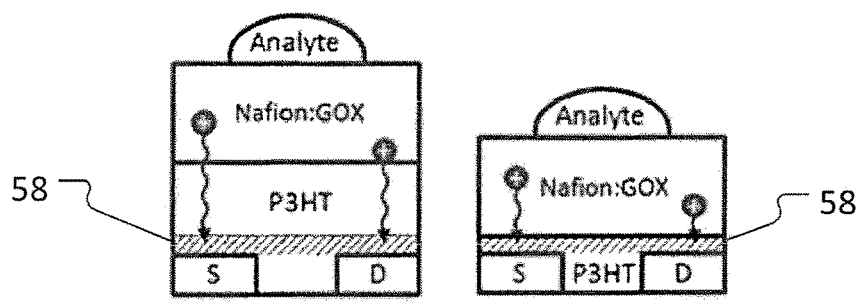
FIG. 4C depicts schematic diagrams showing the location of proposed doping region in the case of a thick P3HT layer and the case of a critical thickness P3HT layer.

Based on this, FIG. 4C depicts schematic diagrams showing the location of the identified doping region (the hatched area 58 in the diagram) for a thick P3HT layer (left hand diagram) and critical thickness P3HT layer (right hand diagram). As the P3HT layer is reduced, it reaches a critical thickness at which the Nafion layer interface is coincident with the doping region and subsequent decreases in P3HT thickness serve only to decrease the size of the doping region and hence the observed current.

Figure 5A:
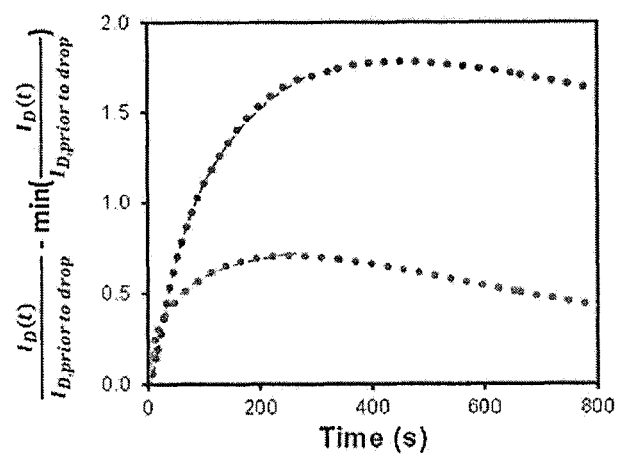
FIG. 5A shows a measure of drain current ($I_D$) vs time for the device according to FIGS. 1 and 2 for two different voltages between (i) ohmic conductor for applying a voltage to the polymer layer and (ii) the drain electrode of the device.
Figure 5B:
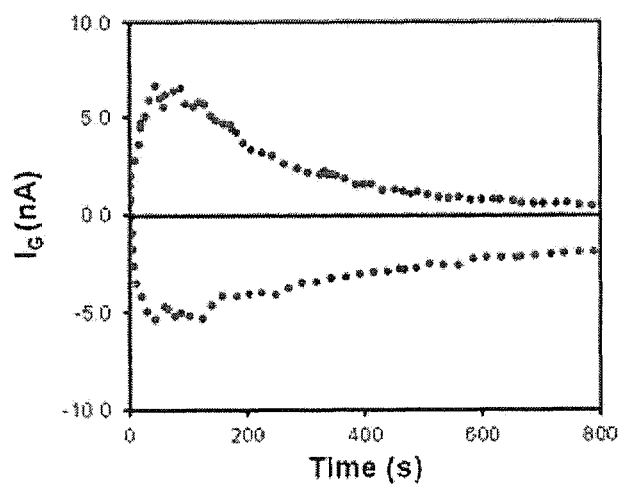
FIG. 5B shows gate current (ie current into the ohmic conductor) as a function of time for the two voltages between the ohmic conductor and drain electrode of the device shown in FIG. 5A.
Figure 5C:
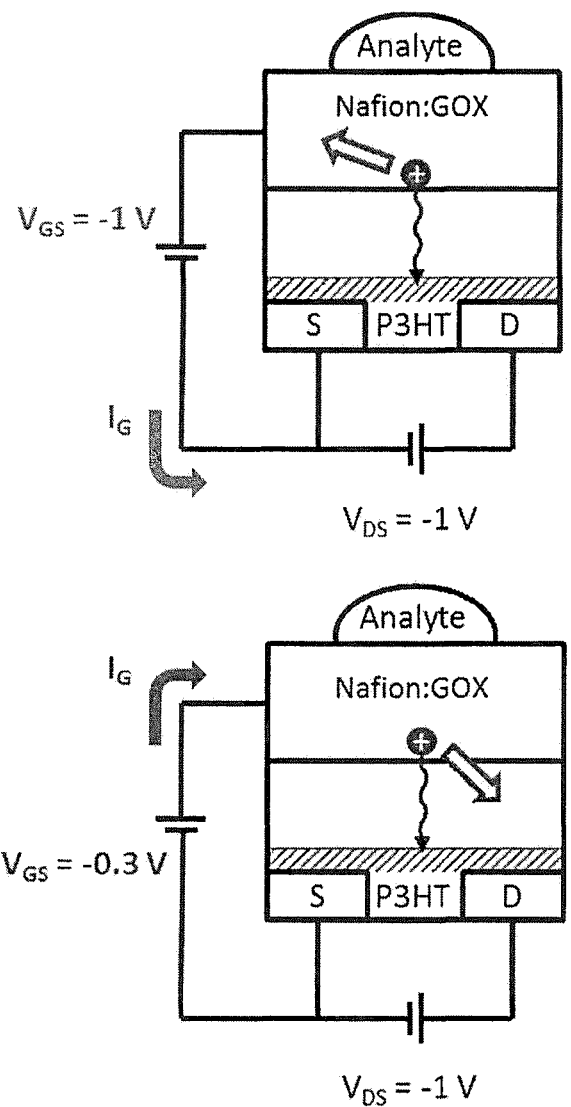
FIG. 5C includes schematic illustrations showing the electric forces act within the device serving to either retard or enhance protonic doping of a semiconductor channel of the device, for the two voltages between the ohmic conductor and drain electrode of the device shown in FIGS. 5A and 5B.

FIGS. 5A-5D shows the effect of changing gate voltage ($V_{GS}$) upon device performance after addition of 30 mM glucose solution. FIG. 5A shows variation of $I_D$ as a function of time for $V_{GS}=-1.0V$ (lower dotted line) and $V_{GS}=-0.3V$ (upper dotted line). This figure shows that as the $V_{GS}$ is made more positive (changed from $-1.0V$ to $-0.3$ V) so the value of adjusted $I_D$ at saturation increases (from about 0.6 to about 1.75 on this scale). FIG. 5B shows variation of gate current as a function of time for $V_{GS}=-1.0V$ (lower dotted line) and $V_{GS}=-0.3V$ (upper dotted line). This figure indicates that this rise in $I_D$ is associated with a change in the polarity of the net current flowing from gate to source. These results are consistent with a change in the net electric field experienced by the charge carriers (protons). When $V_{GS}=-1.0$ V, there is a net electric field from source to gate (since both ohmic conductor 32 and drain electrode 12 are held at $-1.0V$ relative to the source electrode 14), whereas when $V_{GS}=-0.3$ V, there is a net electric field from gate to drain. These electric forces act in addition to the diffusion gradient within the device serving to either retard ($V_{GS}=-1.0$ V) or enhance ($V_{GS}=-0.3$ V) protonic doping of the channel, as shown schematically in FIG. 5C, which indicates the gate current flow and net electric field (unfilled arrows) for $V_{GS}=-1.0V$ and $-0.3$ V. This change in $V_{GS}$ increases the sensitivity of the device response and consequently subsequent measurements discussed hereinafter have been conducted with a gate bias voltage of $-0.3$ V.

The present have identified that to improve consistency of the GOX thickness and to reduce aggregation GOX, the polymer (Nafion) of the polymer layer can be may be spin coated as a first step, and the enzyme (GOX) can be subsequently inkjet-printed onto the polymer.

The inventors attribute this improvement to both the higher solubility of GOX in water compared to a solvent mixture in which GOX is pre-mixed with Nafion and drop-cast together. Additionally or alternatively, the improvement may be due to a slower deposition rate. In devices with inkjet-printed GOX, the enzymatic activity of the devices remained intact, and the response time of the devices improved (conceivably due to diffusion through the thinner spin-coated Nafion layer being a faster process than through the thicker, drop-cast layer, as well as due to the enzyme being more readily available to the analyte, since it is more evenly dispersed). For such devices with a spin-coated Nafion layer and inkjet-printed enzyme, a calibration parameter, X, was calculated from t=0 to 500 s. The parameter X was defined as follows:

$$X = \frac{\int_{t=0}^{\tau=500} I_d(t)dt}{\int_{t=0}^{\tau=500} I_d(0)dt}.$$

Figure 6:
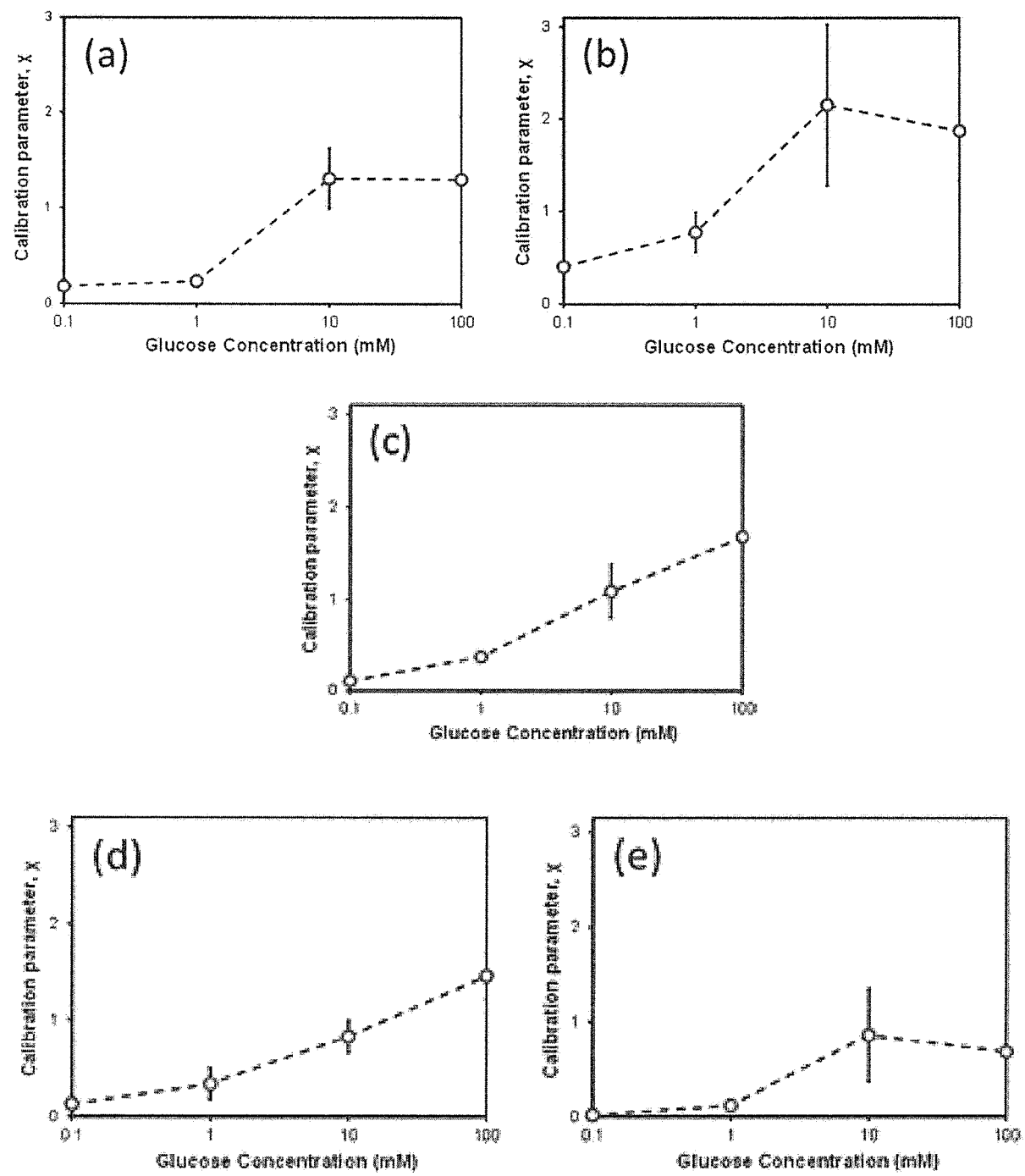
FIG. 6 shows calibration curves for inkjet-printed OTFT sensor devices with P3HT thicknesses varying from 22 nm to 390 nm.

FIG. 6 shows the calibration curves (average calibration parameter, X, as a function of glucose concentration) for inkjet-printed OTFT sensor devices with P3HT thicknesses varying from 22 nm to 390 nm. In particular FIG. 6 shows calibration curves for P3HT thicknesses of: 22 nm (curve a), 36 nm (curve b), 74 nm (curve c), 108 nm (curve d), and 390 nm (curve e).

Although the thinner P3HT devices have a faster response, the results shown in FIG. 6 indicate that variability in the device response to the glucose analyte in solution also increases for thinner P3HT devices, resulting in a reduced linearity of the calibration curve. For embodiments where linearity of the calibration curve is important, the results show that a P3HT thickness of about 74 nm to about 108 nm (eg 75-100 nm) as providing a good balance between glucose sensitivity and reproducibility. As illustrated in curves c and d of FIG. 6, an approximately linear response can be expected between glucose concentration and X for glucose concentrations between 100 μM and 100 mM.

Examples illustrating that the device 10 can operate without a hygroscopic dielectric layer 20 between the polymer layer 30 and semiconductor layer 18 will now be described.

I. Experimental Procedure

Pre-patterned ITO-on-glass substrates (15Ω□$^{-1}$ ITO, Xin Yan Technology) were used for the substrate, the source and drain electrodes and ohmic conductor 32 of the fabricated devices. Poly-3-hexylthiophene (P3HT) (MW ~20 000, synthesised in the labs) was dissolved in CHCl$_3$ (Sigma-Aldrich) at various concentrations and sonicated for ~1 hour or until the material was entirely dissolved. Poly-4-vinylphenol (PVP) (Sigma-Aldrich) was dissolved in ethanol (Sigma-Aldrich) at a concentration of 80 mg mL$^{-1}$ and sonicated for ~1 hour or until the material was entirely dissolved. Nafion solution (5% by weight in lower aliphatic alcohols and water, Sigma-Aldrich) was used as received. Glucose oxidase (GOX) (Sigma) was either mixed with the as received Nafion solution at a concentration of 20 mg mL$^{-1}$ or dissolved in purified water (Milli-Q purification system, Millipore) at a concentration of 50 mg mL$^{-1}$ prior to processing. Glucose (Sigma-Aldrich) was dissolved in purified water at various concentrations.

The pre-patterned ITO-on-glass substrates were first cleaned with methanol and purified water. P3HT solution in CHCl$_3$ was spin-coated onto the substrates at 2000 rpm for 60 seconds. P3HT solutions of 5 mg mL$^{-1}$, 10 mg mL$^{-1}$, 15 mg mL$^{-1}$, 20 mg mL$^{-1}$, and 40 mg mL$^{-1}$ were prepared, with average thicknesses of films spun from these concentrations of P3HT were 22 nm, 36 nm, 74 nm, 108 nm and 390 nm respectively. The P3HT layer was patterned and then left to dry for 15 minutes at 40° C. For devices with a PVP layer, PVP solution was then spun on top of the P3HT layer at 2000 rpm for 60 seconds (film thickness ~400 nm), then patterned and dried. For these PVP-containing devices, the Nafion:GOX mixture was then drop-cast above the source-drain channel area and connected to the ITO gate pad of the substrate and dried for approximately 30 minutes. This drop-cast Nafion:GOX layer allows protonic conduction. For the first devices in which the Nafion and GOX were deposited independently, Nafion solution was first spin-coated at 500 rpm for 120 seconds. Subsequently, the aqueous GOX solution was either drop-cast or inkjet-printed above the source-drain channel area to enable a comparison between these two different methods of device preparation.

Inkjet-printed GOX was deposited using a Fujifilm Dimatix DMP 2800 piezoelectric inkjet-printer. 2 mL of the aqueous GOX solution was injected into a cartridge (DMC 11610, Fujifilm Dimatix). GOX solution was printed onto a ~7 mm$^2$ area over the channel of each device, and was then dried on a hotplate at 40° C. The printing conditions were: 20 μm drop spacing, 10 layers, 28° C. platen heating, ~25 V drive voltage, jetting frequency 2 kHz.

For measurements of drain current ($I_D$) and gate current ($I_G$) versus time for various glucose concentrations, two Keithley 2400 source meters were used to collect the data with the source electrode considered as the common electrode (0 V) and the drain voltage ($V_{DS}$) held at −1 V. Gate voltage ($V_{GS}$) was held at either −0.3 V or −1 V (see discussion below). After time to allow $I_D$ to stabilise, 5 μL of an aqueous glucose solution was dropped on top of each device, immediately above its source-drain channel. Glucose concentrations between 100 μM and 100 mM were used in this study, with $I_D$ and $I_G$ being recorded for a further 10 minutes after addition of the analyte solution. Film thickness measurements were taken using a Tencor Alpha-Step 500 surface profilometer.

III. Characterization of Sensors with and without PVP Layer

Figure 7A:
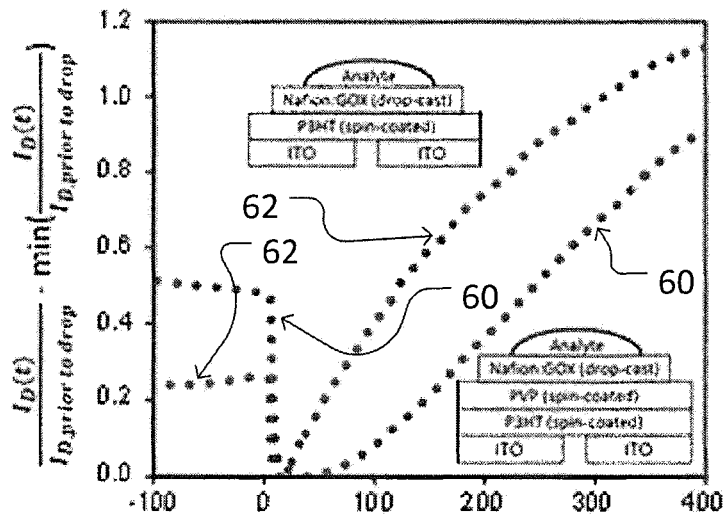
FIG. 7A to 7C a measure of drain current ($I_D$) vs time for the device according to FIGS. 1 and 2, comparing the case of having a PVP dielectric layer with not having a PVP dielectric layer.
Figure 7B:
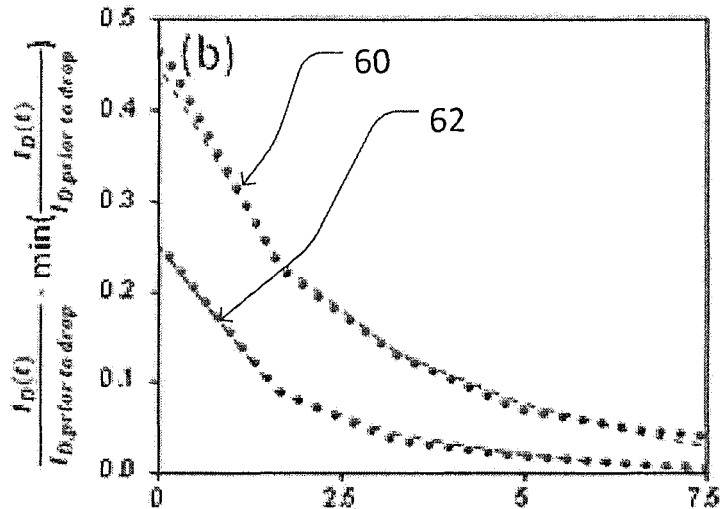
Figure 7C:
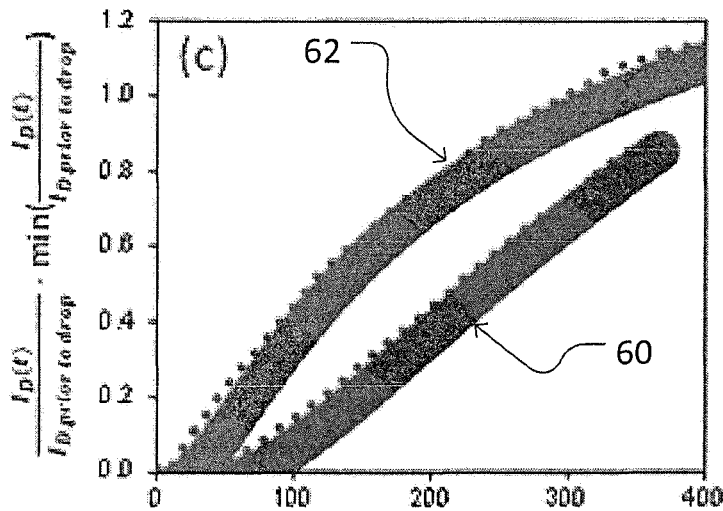

FIG. 7A shows the $I_D$ versus time characteristics of devices prepared with the standard architecture (P3HT/PVP/Nafion:GOX), indicated by curve 60, and without the PVP layer (P3HT/Nafion:GOX), indicated by curve 62, to a drop of 30 mM glucose analyte solution; revealing operation og the two time dependent processes discussed above. Specifically, there is firstly a rapid drop in $I_D$ upon addition of the analyte solution to the Nafion gate electrode at time t=0 (best seen in FIG. 7B). This process is independent of glucose concentration and arises from dedoping of the P3HT channel since it also occurs upon the addition of deionised water alone. Second, there is a much slower rise in drain current (best seen in FIG. 7C) that is correlated with glucose concentration and thus defines the functional response time of the sensor. This slower process arises from protonic diffusion and doping of the P3HT channel. As discussed above, both processes can be modelled by one dimensional solutions to Fick's second law of diffusion, n (x,t)=n$_0$ erfc{x/[2(D$_{eff}$t)$^{0.5}$]}=n$_0$ erfc(A/t$^{0.5}$), where A (comprising x (diffusion distance) and D$_{eff}$ (effective diffusion constant)) and n$_0$ (initial concentration), are treated as fitting constants with the fit solution shown as dashed lines in FIG. 7B and FIG. 7C. The fitted values of A are: 0.9 (with PVP) and 0.62 (without PVP) for the fast decay process. The fitted values of A are: 18 (with PVP) and 10.3 (without PVP) for the slow decay process. Elimination of the PVP layer reduces the response time of both processes, consistent with diffusion processes that traverse a reduced layer thickness. The data highlights that the PVP layer is not required for device function and serves only to slow the device response.

III. Optical Microscopy and Profilometry of Spin Coated and Inkjet-Printed GOX-Containing Layers FIGS. 8A-E shows profilometry and microscopy of both the inkjet-printed and drop-cast Nafion:GOX layers. FIG.

Figure 8A:
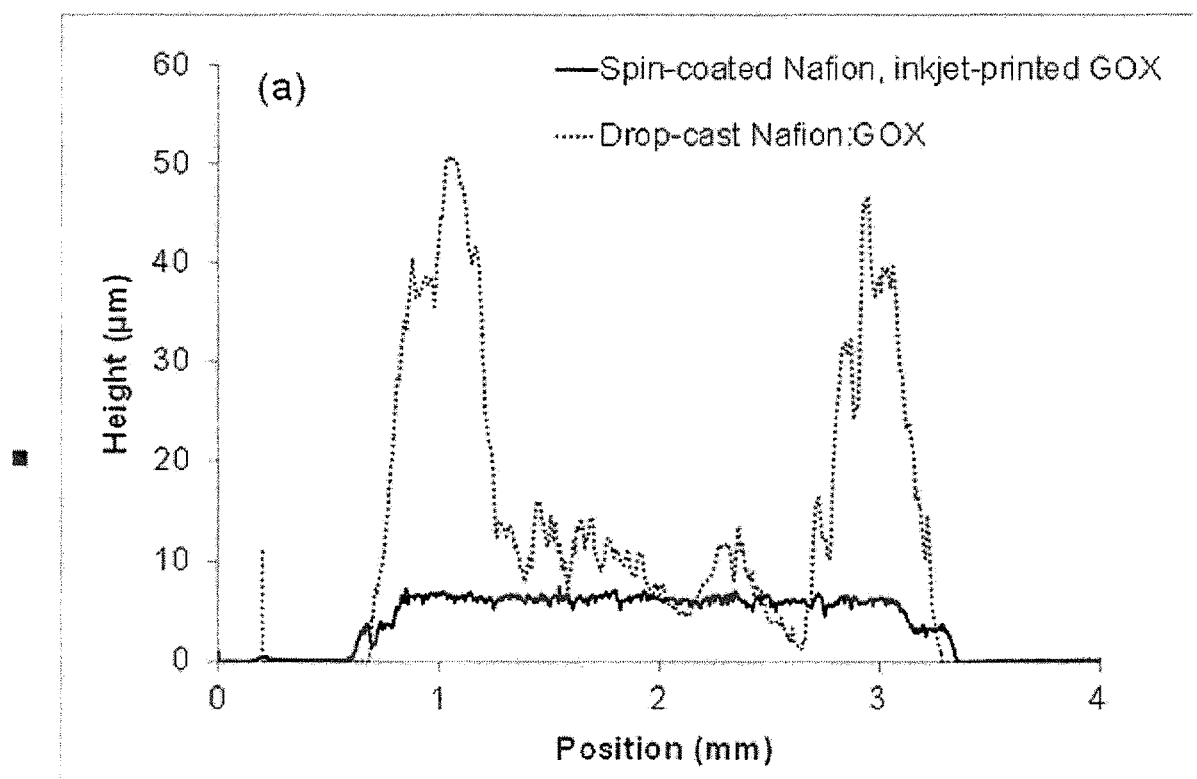
FIG. 8A shows profilometry for the device according to FIGS. 1 and 2 comparing layers made from (a) inkjet-printed GOX on spin coated Nafion and (b) drop-cast Nafion:GOX.
Figure 8B:
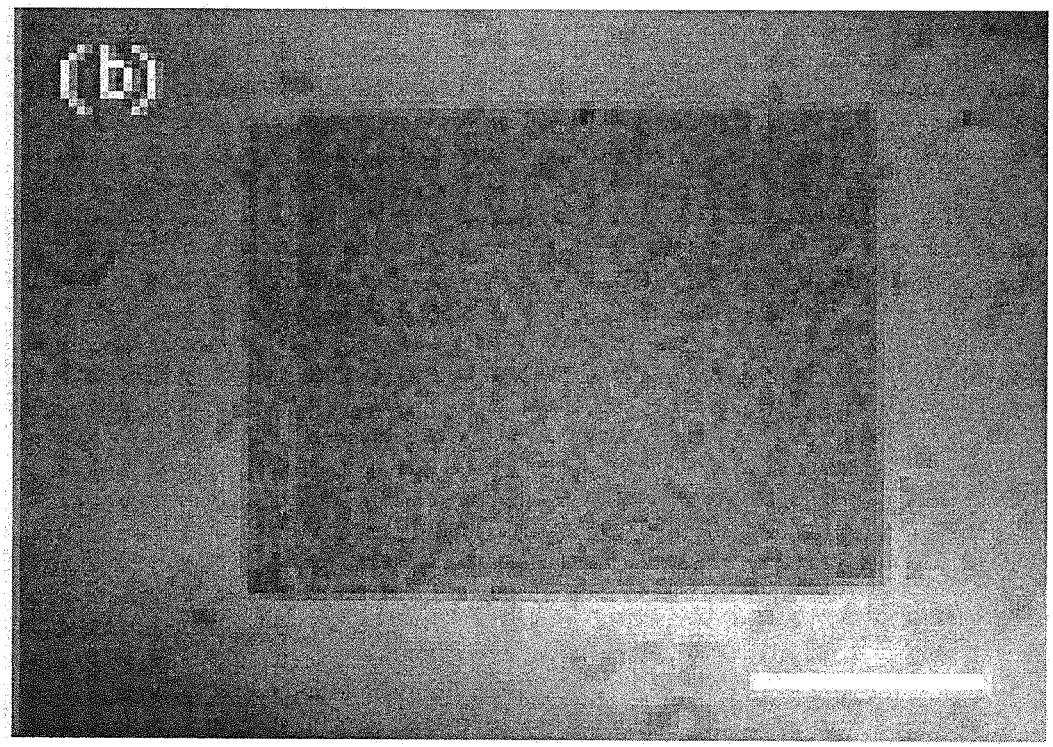
FIGS. 8B-8E shows microscopy for the device according to FIGS. 1 and 2 layers made from (a) inkjet-printed GOX on spin coated Nafion and (b) drop-cast Nafion:GOX.
Figure 8C:
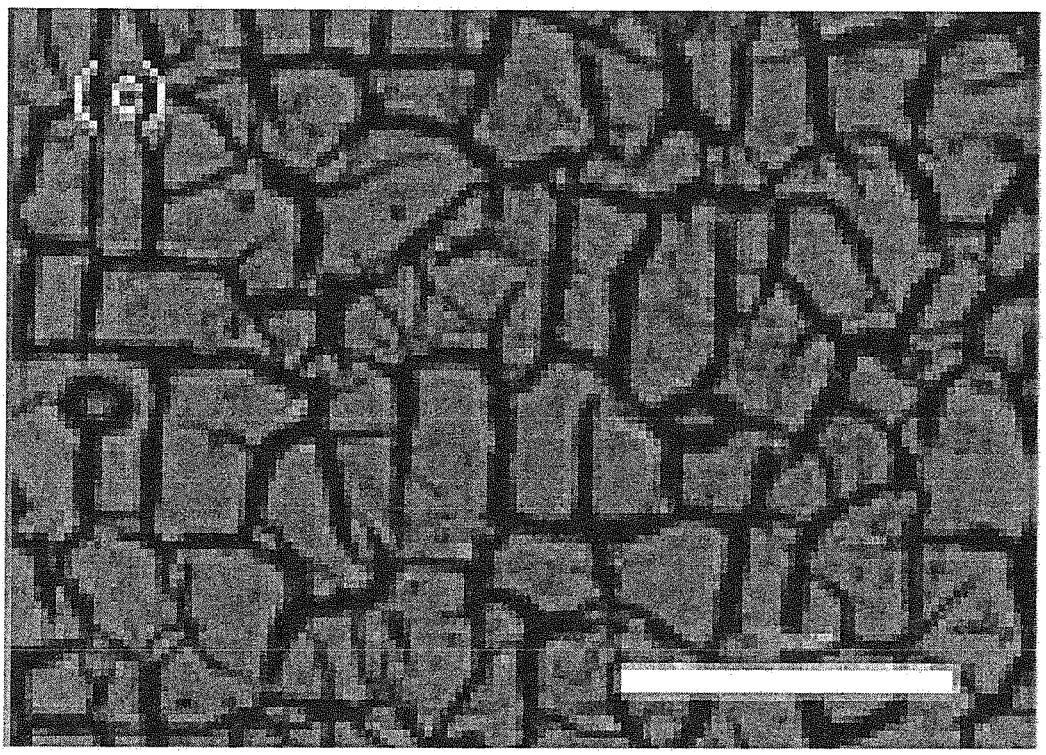
Figure 8D:
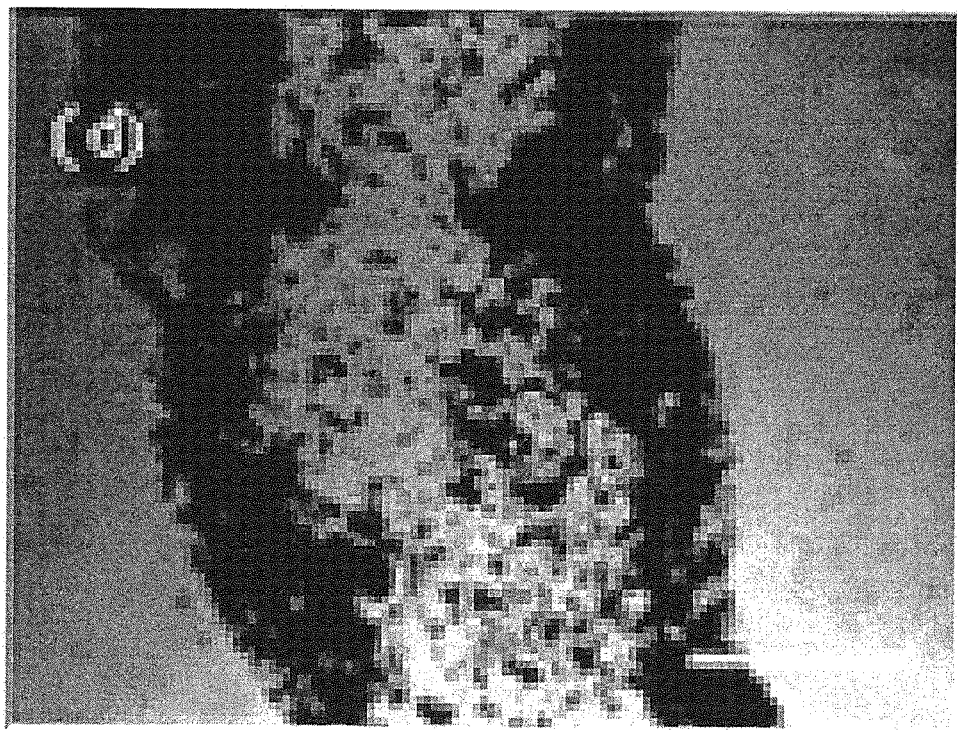
Figure 8E:
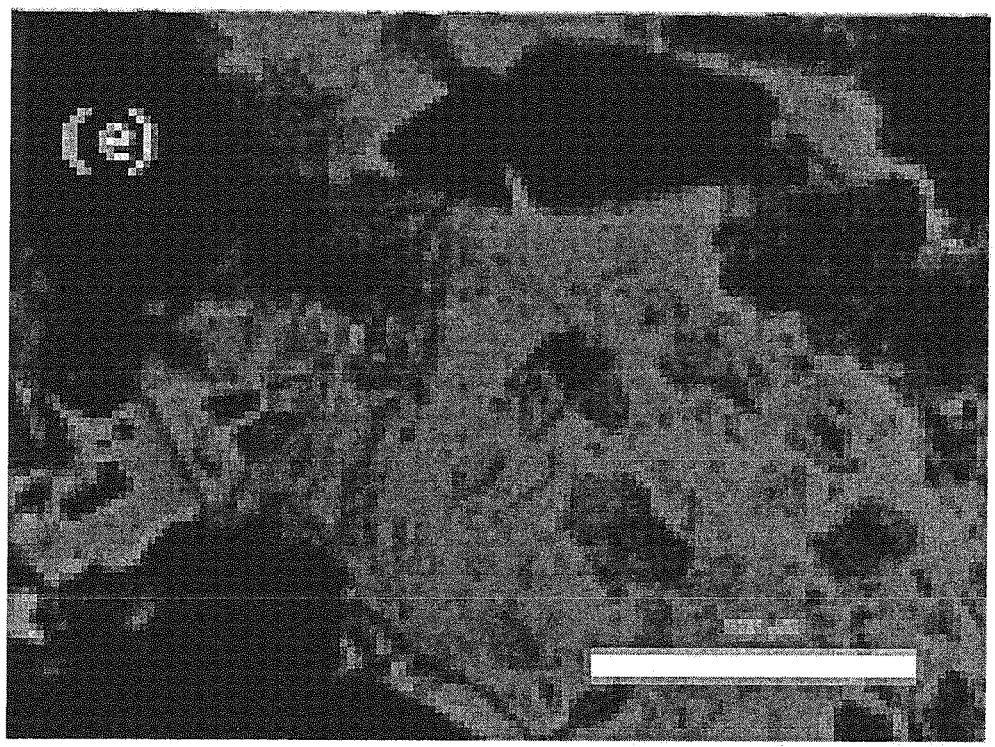

8A shows profilometry of regions of both inkjet-printed GOX on spin-coated Nafion and drop-cast GOX:Nafion mixture. The profilometry in FIG. 8A reveals a dramatic decrease in the surface roughness of the inkjet-printed GOX layer compared to the drop cast films suggesting a much more even distribution of the enzyme. FIGS. 8B and 8C show optical micrographs of a region of GOX inkjet-printed on a spin-cast Nafion layer (scale bars are 1 mm and 100 μm respectively). FIGS. 8D and 8E show optical micrographs of a region of drop-cast Nafion:GOX mixture (scale bars are 1 mm and 100 μm respectively). The microscopy results in FIGS. 8B to 8E confirm that the inkjet-printed devices are much more uniform across the entire area of the film.

IV. Example Data—ID Vs Time for a Range of Glucose Concentrations

Figure 9:
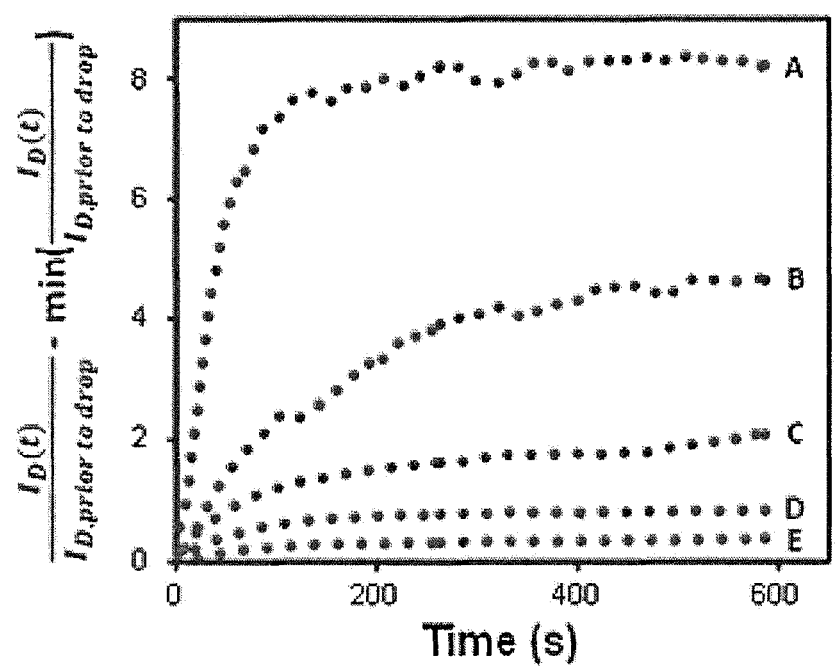
FIG. 9 shows the response of devices with a spin-coated Nafion film and inkjet-printed GOX to range of glucose analyte concentrations (0 to 100 mM)

FIG. 9 shows the response of devices with a spin-coated Nafion film and inkjet-printed GOX to range of glucose analyte concentrations (0 to 100 mM). The figure shows adjusted drain current as a function of time for OTFT devices with different glucose analyte concentrations: 100 mM (curve A), 10 mM (curve B), 1 mM (curve C), 0.1 mM (curve D) and 0 mM (curve E). FIG. 9 reveals two key features. First, it is clear that the activity of the GOX has remained after inkjet-printing; demonstrating that the enzyme activity is retained even after the fabrication process. Second, the rise time of the devices is now much faster than observed for drop-cast devices 13 and thus much more responsive devices have been fabricated using the inkjet-printing approach. It is also possible that the reoxidation of the reduced GOX may not be very efficient and that this process is limiting the response of the devices. As such, further improvements in sensor response may be possible by increasing oxygen accessibility in the device.

V. Example Data—OTFT Output Characteristics

Figure 10:
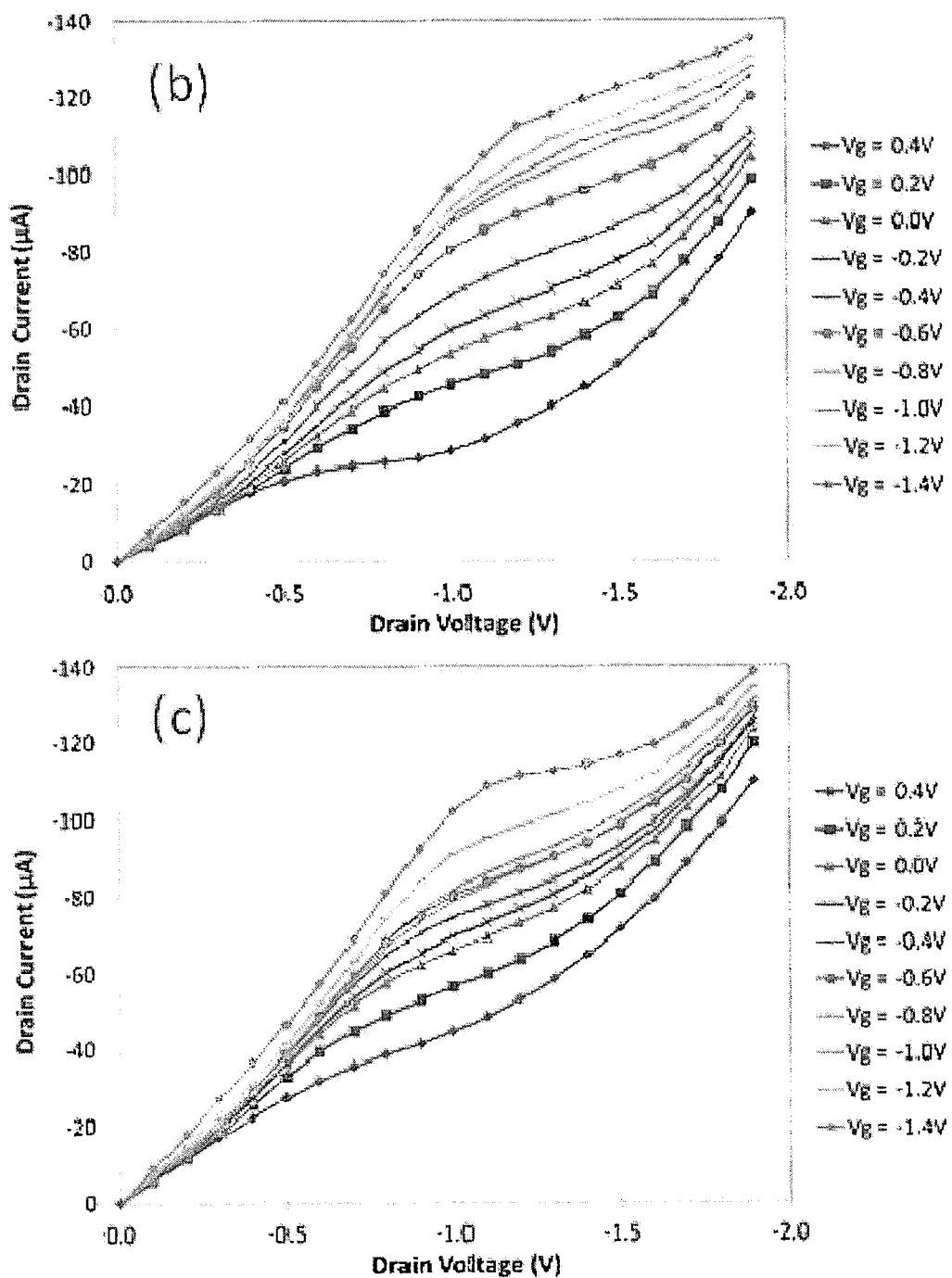
FIG. 10 shows measured OTFT output characteristics for the device according to FIGS. 1 and 2, comparing the case of having a PVP dielectric layer with not having a PVP dielectric layer.

In FIG. 10, sets of curves labelled b and c show the output characteristics for the PVP-containing sensor device and the PVP-free sensor device prior to inkjet-printing of the enzyme, respectively. In each of curve sets, the lowest curve represents $V_G$=4V, and the highest curve represents $V_G$=−1.4V. As can be seen from these figures, each of these devices exhibit drain current modulation with changes in gate voltage.

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. A transistor device comprising:
   a source electrode;
   a drain electrode;
   an enzyme for facilitating generation of a charge carrier from an analyte;
   a polymer layer for retaining the enzyme, the polymer layer being conductive to the charge carrier;
   an ohmic conductor in contact with said polymer layer for applying a gate voltage to said polymer layer; and
   an organic semiconducting layer in contact with said polymer layer, the organic semiconducting layer connecting the source electrode to the drain electrode.

2. A transistor according to claim 1, wherein a layer of the enzyme is formed on a surface of the polymer layer.

3. A transistor according to claim 1, wherein neither said polymer layer nor said semiconducting layer include poly (4-vinylphenol) (PVP).

4. A device according to claim 1, wherein organic semiconductor layer has a thickness of less than about 390 nm.

5. A device according to claim 1, wherein the organic semiconductor layer has a thickness of between about 36 nm and about 9 nm.

6. A device according to claim 1, wherein the organic semiconductor layer has a thickness between about 74 nm and about 108 nm.

7. A device according to claim 1, wherein the carrier is a proton.

8. A device according to claim 1, wherein said polymer layer forms a proton-conductive membrane.

9. A device according to claim 1, wherein the polymer layer has a conductivity to protons that is greater than a conductivity to protons that is possessed by said organic semiconductor layer.

10. A device according to claim 1, wherein at least part of the polymer layer is disposed above the semiconductor layer with respect to a substrate layer.

11. A device according to claim 1, wherein at least part of the ohmic conductor is disposed beneath part of the polymer layer.

12. A device according to claim 1, wherein the enzyme is glucose oxidase for detecting glucose in saliva.

13. A device according to claim 1, wherein the organic semiconductor comprises, consists, or consists essentially of at least one organic compound that has semiconducting properties, the at least one organic compound being any one or more of: polyacetylenes, porphyrins, phthalocyanins, fullerenes, polyparaphenylenes, polyphenylenevinylenes, polyfluorenes, polythiophenes, polypyrroles, polypyridines, polycarbazoles, polypyridinevinylenes, polyarylvinylenes, poly (p-phenylmethylvinylenes), including derivatives and co-polymers thereof, and further including mixtures thereof.

14. A device according to any one of claim 13, wherein the at least one organic compound is poly(3-hexyl-thiophene), ie P3HT.

15. A device according to claim 1, wherein the polymer layer comprises, consists, or consists essentially of a sulfonated tetrafluoroethylene-based fluoropolymer-copolymer.

16. A device according to claim 15, wherein the sulfonated tetrafluoroethylene-based fluoropolymer-copolymer is a tetrafluoroethylene-perfluoro-3,6-dioxa-4-methyl-7-octenesulfonic acid copolymer.

17. A method for preparing a transistor device as defined in claim 1, the method comprising:
   a) providing a substrate for depositing thereon components of the device;
   b) depositing the source electrode and the drain electrode;
   c) depositing the organic semiconductor;
   d) depositing the polymer; and
   e) depositing the enzyme on said polymer.

18. A method for preparing a transistor device according to claim 17, wherein step b) precedes step c), step c) precedes step d), and step d) precedes step e).

19. A method for preparing a transistor device according to claim 17, wherein the enzyme after step d).

20. A method for preparing a transistor device according to claim 17, wherein the enzyme is introduced by ink-jet printing.

21. A method for preparing a transistor device according to claim 17, wherein the semiconductor layer is deposited by spin coating.

22. A method for preparing a transistor device according to claim 17, wherein the polymer layer is deposited by spin coating.

23. A method for detecting and/or determining a concentration or an amount of an analyte in a sample, the method comprising the following steps:
- a) providing a device of claim 1;
- b) contacting the sample with the device; and
- c) detecting and/or determining the concentration or the amount of the analyte based on an electrical parameter of the device.

24. A transistor device comprising:
- a source electrode;
- a drain electrode;
- an enzyme for facilitating generation of a charge carrier from an analyte;
- a polymer layer for retaining the enzyme, the polymer layer being conductive to the charge carrier;
- an ohmic conductor in contact with said polymer layer for applying a gate voltage to said polymer; and
- an organic semiconductor layer connecting the source electrode to the drain electrode;
- wherein a layer of the enzyme is formed on a surface of the polymer layer.

* * * * *